United States Patent
Grenaway et al.

(10) Patent No.: US 8,028,712 B2
(45) Date of Patent: Oct. 4, 2011

(54) DIAPHRAGM CONTROLLED BYPASS VALVE

(75) Inventors: John R. Grenaway, Edwardsville, IL (US); Mark K. Hamm, Cullman, AL (US); William Clinton Osteen, Hartselle, AL (US)

(73) Assignee: Tyco Valves & Controls LP, Houston, TX (US)

( * ) Notice: Subject to any disclaimer, the term of this patent is extended or adjusted under 35 U.S.C. 154(b) by 520 days.

(21) Appl. No.: 12/168,272

(22) Filed: Jul. 7, 2008

(65) Prior Publication Data
US 2009/0278065 A1    Nov. 12, 2009

Related U.S. Application Data

(63) Continuation-in-part of application No. 12/117,524, filed on May 8, 2008.

(51) Int. Cl.
*G05D 11/00* (2006.01)
(52) U.S. Cl. .................. 137/116.5; 251/77
(58) Field of Classification Search .......... 251/77; 137/87.01, 118.06, 115.13, 115.26, 116.3, 137/116.5
See application file for complete search history.

(56) References Cited

U.S. PATENT DOCUMENTS

| 2,181,428 | A | * | 11/1939 | Grove | 137/509 |
| 3,468,339 | A | * | 9/1969 | Gray | 137/625.4 |
| 3,468,341 | A | * | 9/1969 | Newcomb et al. | 137/625.3 |
| 3,470,910 | A | | 10/1969 | Loveless | |
| 3,578,019 | A | | 5/1971 | Turolla | |
| 3,848,630 | A | | 11/1974 | Weise | |
| 3,892,389 | A | | 7/1975 | Contastin | |
| 4,624,277 | A | * | 11/1986 | Veite | 137/116.3 |
| 4,942,899 | A | * | 7/1990 | Vork et al. | 137/454.5 |
| 5,467,754 | A | | 11/1995 | Beck et al. | |
| 5,800,381 | A | | 9/1998 | Ognier | |
| 6,554,017 | B2 | * | 4/2003 | Berger | 137/116.5 |
| 2007/0137705 | A1 | * | 6/2007 | Chen | 137/115.13 |

FOREIGN PATENT DOCUMENTS

GB         363114    A1    12/1931

* cited by examiner

*Primary Examiner* — John Fristoe, Jr.
*Assistant Examiner* — Marina Tietjen

(57) ABSTRACT

A diaphragm controlled bypass valve includes a diaphragm valve portion and a needle valve portion. The diaphragm valve portion regulates pressurized gas supplied from a pump to determine whether or not to open or close a needle valve. The needle valve portion includes an inlet port, an outlet port and a flow pathway defined between the inlet and outlet ports. A needle pin is disposed within the flow pathway and is coupled to a diaphragm positioned within the diaphragm valve portion. When the diaphragm is displaced in response to changes in pressure, the needle valve pin is likewise displaced which opens and closes the flow pathway. A second flowpath disposed in the needle valve portion communicates with the inlet port to redirect the supply of pressurized gas to a relief port.

14 Claims, 7 Drawing Sheets

DIAPHRAGM CONTROLLED BYPASS VALVE

This patent application is a continuation-in-part of co-pending U.S. application Ser. No. 12/117,524, filed May 8, 2008. The aforementioned patent application is incorporated by reference herein in its entirety.

FIELD OF THE INVENTION

Embodiments of the invention relate to the field of valves and the construction thereof. More particularly, embodiments of the invention relate to a diaphragm controlled bypass valve used to regulate the flow of gas from an external source.

DISCUSSION OF RELATED ART

In laparoscopic surgery, a device such as a trocar is used to introduce various surgical instruments into a patient's abdomen. An insufflating gas, for example $CO_2$, is also introduced into the abdominal cavity to raise the cavity wall away from vital organs to avoid any unnecessary contact during the surgical procedure. This gas is usually supplied by a pump or gas source at a pressure of about 25 psi and is supplied to a patient's abdomen using a flexible tube or conduit. A Verres needle inserted into a patient's abdominal cavity supplies the gas from the pump to the abdomen which is maintained at a pressure of about 10-12 mmHG. The pressurized gas supplied to the abdominal cavity is monitored to ensure that pressure within the cavity is maintained within a desired pressure range. Pressure changes in a patient's abdominal cavity during surgery may be as small as ±1 mmHG. Existing systems do not detect these small pressure changes in the abdominal cavity nor do they automatically adjust the flow of gas to the abdomen based on such changes.

Pressure regulators in the form of diaphragm valves utilize an extended membrane to open and close a flow pathway. These valves have moveable diaphragms to control process flow, such as a gas, and are commonly used for processing systems used in pharmaceutical, biotechnical, chemical, food, and semiconductor industries. Although diaphragm valves are reliable and sensitive to slight variations in pressure, they are usually only configured to open and close at certain pressure levels. That is, when a particular pressure level is reached the valve either opens or closes. The objective in the above-referenced surgical procedure is to regulate the flow of pressurized gas to maintain insufflation of a patient's abdomen. In these applications, the valve which controls the flow of pressurized gas to the surgical device typically remains in an open position to regulate the amount of pressurized gas to the system. Accordingly, a valve employed in these systems must be configured to remain in an open position and regulate the amount of pressurized gas to a patient's abdomen. These systems typically monitor the supply line gas pressure coming from the pump or gas source to the surgical device rather than monitoring a patient's abdominal pressure. When the abdominal pressure falls below a desired level, the valve must be configured to react quickly to allow pressurized gas to flow to the surgical device to increase pressure in the patient's abdomen. In addition, when the abdominal pressure increases above a desired level the valve must be configured to react quickly and allow pressurized gas to be diverted away from a patient's abdomen. Thus, there is a need for a valve that maintains a desired pressure range while being sensitive enough to respond rapidly to pressure changes during surgical procedures. There is also a need for a valve to control the flow of pressurized gas from a pump or gas source based on a patient's abdominal pressure rather than supply line pressure.

SUMMARY OF THE INVENTION

Exemplary embodiments of the present invention are directed to a diaphragm controlled bypass valve. In an exemplary embodiment, the diaphragm controlled bypass valve includes a first valve housing having an inlet, an outlet and a flow pathway defined between the inlet and the outlet. A needle valve pin is disposed at least partially within the flow pathway. A valve seat is disposed within the first valve housing and is configured to receive a portion of the needle valve pin to close the flow path. A second valve housing is connected to the first valve housing. A diaphragm extends radially within the second valve housing. A first pressure chamber is defined between the diaphragm and the second valve housing. A second pressure chamber is defined between the diaphragm and the first valve housing. A sensing line is connected to the second pressure chamber and is configured to provide a pressure change to the second pressure chamber to displace the diaphragm within the first pressure chamber. A shaft assembly is disposed between the diaphragm and the needle pin such that displacement of the diaphragm within the second pressure chamber moves the shaft to open and close the needle valve.

DESCRIPTION OF EMBODIMENTS

Figure 1:
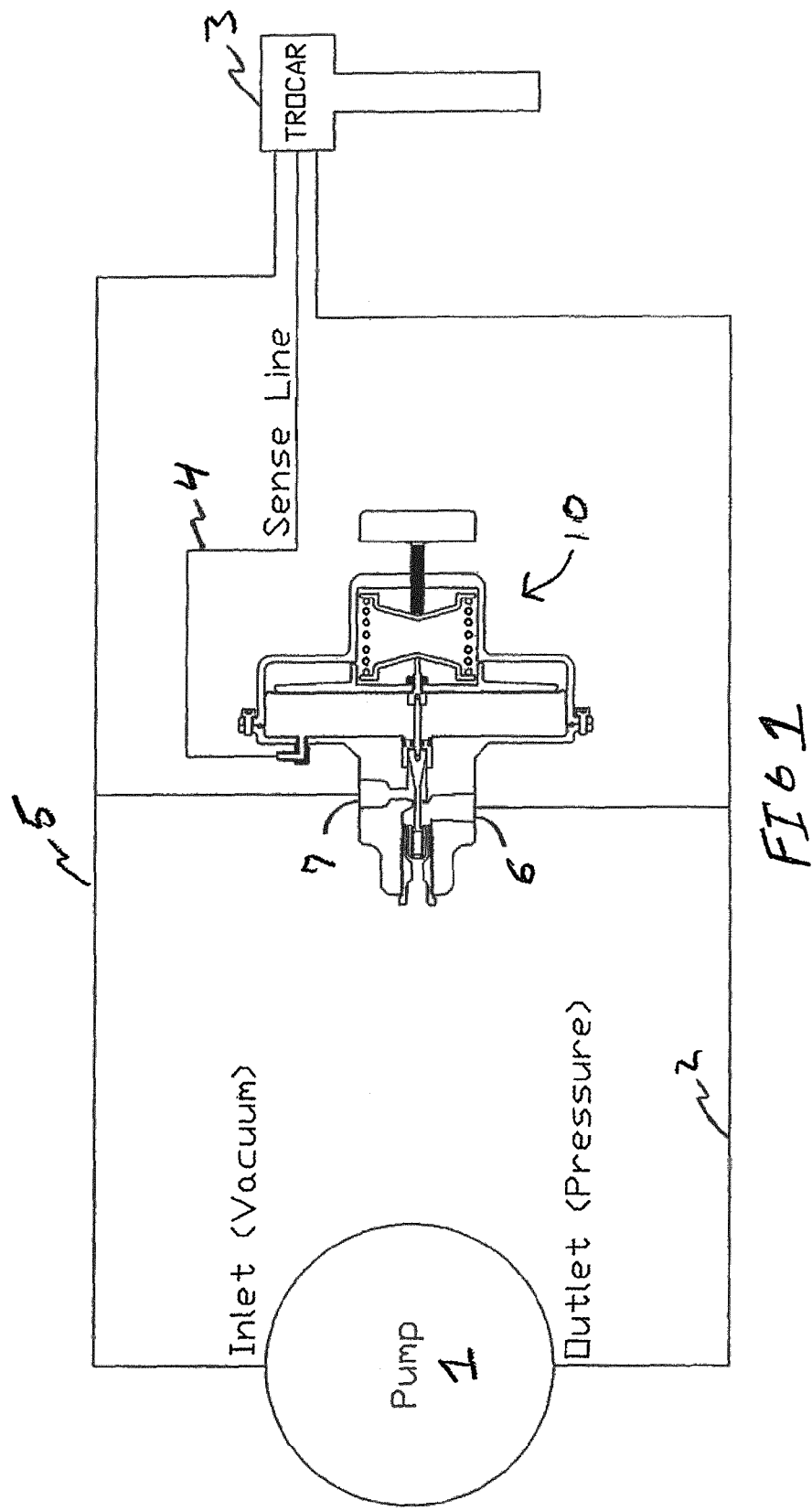
FIG. 1 is a block diagram of a diaphragm controlled bypass valve positioned within an exemplary surgical application in accordance with the present invention.

The present invention will now be described more fully hereinafter with reference to the accompanying drawings, in which preferred embodiments of the invention are shown. This invention, however, may be embodied in many different forms and should not be construed as limited to the embodiments set forth herein. Rather, these embodiments are provided so that this disclosure will be thorough and complete, and will fully convey the scope of the invention to those skilled in the art. In the drawings, like numbers refer to like elements throughout.

FIG. 1 is a schematic representation of an embodiment of the present invention disposed in a surgical application for example, an insufflation system utilizing a trocar device for laparoscopic surgical procedures. Typically, a gas supply or pump 1 provides pressurized gas (for example $CO_2$) via conduit 2 to an input port 6 of bypass valve 10. Bypass valve 10 is connected in parallel with surgical device 3 and regulates the flow of such gas from supply 1 to surgical device 3. Surgical device 3 directs outlet gas to an inlet or vacuum port of pump 1 via return line 5 which is likewise connected to outlet port 7 of valve 10. Thus, the system provides pressurized gas to a patient's abdomen using a closed system.

As noted above, laparoscopic surgical procedures utilize pressurized gas supplied to a patient's abdominal cavity. A sensing line 4 is connected between the surgical device 3 and bypass valve 10 to detect changes in this abdominal pressure. Bypass valve 10 is used to balance or regulate the flow of pressurized $CO_2$ gas to a patient's abdomen via surgical device 3 or a separate apparatus used to provide pressurized gas to a patient's abdomen. In particular, abdominal pressure values during surgical procedures vary, but may be within the range of 8-15 mmHG. Bypass valve 10 may be configured to allow a certain amount of pressurized gas from pump 1 to flow to the abdominal cavity via surgical device 3 to maintain the desired pressure value. By regulating the amount of gas bypassed from inlet port 6 to outlet port 7, a desired amount of pressurized $CO_2$ is supplied from pump 1 to surgical device 3. Bypass valve 10 maintains the supply of pressurized gas to the abdominal cavity and detects pressure changes of approximately ±1 mmHG. As the pressure in the abdominal cavity increases to unsafe levels outside an acceptable range, sensing line 4 provides an increase pressure supply to bypass valve 10. An increase in pressure may be caused by, for example, the introduction of laparoscopic instruments into a patient's abdomen. This initiates bypass valve 10 to open further which bypasses pressurized gas from pump 1 through valve 10 via input port 6 to output port 7. In this manner, pressurized gas from pump 1 is diverted away from surgical device 3 through bypass valve 10 back to pump 1, thereby reducing the supply of pressurized gas to a patient's abdomen. Conversely, as the pressure in the abdominal cavity decreases below an acceptable range, sensing line 4 provides a reduced pressure supply to bypass valve 10. This initiates bypass valve 10 to close further reducing the flow of gas from inlet port 6 to outlet port 7 and directing more pressurized gas to surgical device 3. In this manner, the supply of pressurized gas from pump 1 to surgical device 3 via bypass valve 10 is regulated to maintain a desired insufflation pressure.

Figure 2:
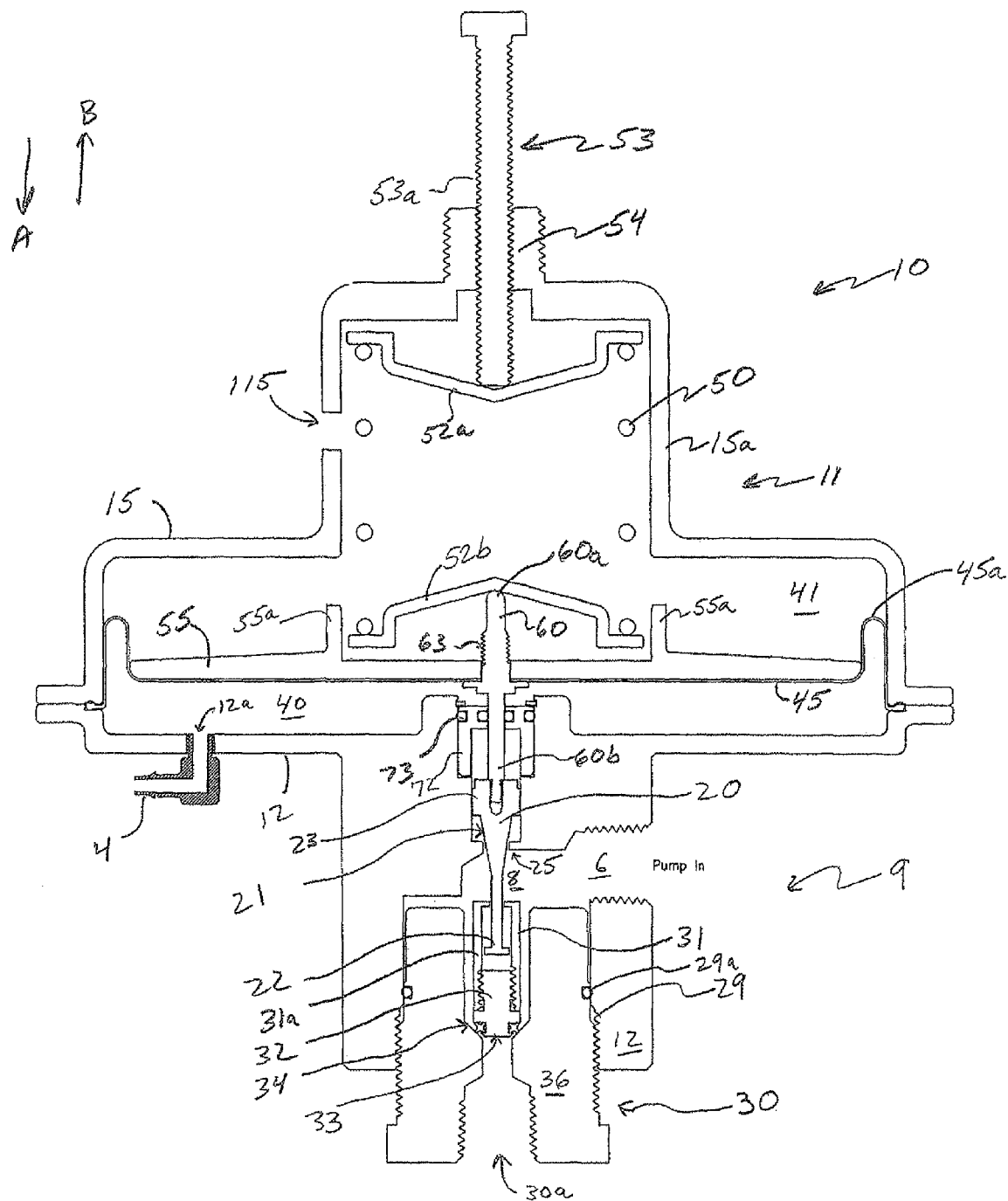
FIG. 2 illustrates a cross sectional view of a diaphragm controlled bypass valve in accordance with the present invention.

FIG. 2 is a cross sectional view of an embodiment of the diaphragm controlled bypass valve 10 generally defined by a needle valve portion 9 and a diaphragm valve portion 11. Needle valve portion 9 includes housing 12 and diaphragm portion 11 includes housing 15 each of which have a substantially circular perimeter. Needle valve housing 12 is connected to diaphragm valve housing 15 to provide an air tight chamber 40 between the valve housings.

Needle valve portion 9 includes an inlet port 6 and valve pathway 8 through needle valve housing 12. Inlet port 6 and outlet port 7 (shown in FIG. 4) define the opening and closing of bypass valve 10. Needle valve portion 9 further includes a valve closure mechanism in the form of needle valve pin 20 which is disposed vertically within valve pathway 8. Pin 20 is defined by angled central portion 21, proximal end 22 and distal end 23. Angled central portion 21 communicates circumferentially with valve seat area 25 of housing 12 to define an opening and closing of needle valve 9. For example, FIG. 2 illustrates bypass valve 10 in an open position such that angled portion 21 of pin 20 is displaced upward and off valve seat 25. As pin 20 moves off seat 25, pressurized gas flows from input port 6 through pathway 8 to output port 7 shown in FIG. 4. In this manner, a portion of pressurized gas from pump 1 supplied to bypass valve 10 is bypassed away from surgical device 3 and returns to the inlet side of pump 1.

Bypass valve 10 also includes an automatic relief mechanism assembly 30 threadedly disposed within aperture 30a of needle valve housing 12. Automatic relief mechanism is configured to rapidly bypass pressurized gas supplied from pump 1 if the pressure in a patient's abdomen gets exceedingly high and a bypass port, in addition to outlet port 7, is required to redirect the supply of pressurized gas. Assembly 30 includes a threaded housing 36 which receives piston 31. Threaded housing 36 is engaged by lower threaded portion 29 of valve housing 12 and the position of housing 36 within aperture 30a may be customized by tightening assembly 30 within valve housing 12. An o-ring 29a may also be positioned between threaded housing 36 and housing 12 to provide a seal therebetween. Piston 31 is defined by a vertical wall 31a and plug 32 having a transverse angled lower wall 33. Plug 32 may be threadedly engaged with vertical wall 31a of piston 31. Proximal end 22 of needle valve pin 20 is positioned within piston 31 and more particularly within the space formed by vertical wall 31a and transverse lower wall 33. Transverse angled lower wall 33 of plug 32 contacts corresponding angled seat 34 of housing 36 to create a seal there between to close aperture 30a. The position of assembly 30 within aperture 30a may be modified by threading assembly 30 upward in direction B within needle housing 12 to accommodate a particular pressure setting or application. This in-turn varies the displacement of proximal end 22 of pin 20 within piston 31. Needle valve housing 12 further includes a bore 12a through which sensing line 4 is connected. As stated earlier, sensing line 4 supplies pressure from surgical instrument 3 to chamber 40.

Diaphragm valve portion 11 is defined by housing or spring chamber 15 which includes diaphragm 45, spring coil 50 and pressure plate 55. Within housing 15, chamber 41 also includes spring plates 52a and 52b disposed at a top and bottom end, respectively of spring coil 50. Diaphragm 45 may be, for example, a convoluted diaphragm disposed between and extending around the circumference of housing 15 and is attached thereto between diaphragm housing 15 and needle housing 12 to create a seal between chambers 40 and 41. Diaphragm 45 is disposed between pressure plate 55 and coupler 60 and has a surface area, for example, of 20 $in^2$. Of course, alternative diaphragm sizes and configurations may be used to accommodate various pressure sensitivities. The diameter and surface area of diaphragm 45 is typically greater than the diameter of housing 15 such that diaphragm portion 45a is folded upward toward chamber 41. This portion 45a or a portion thereof is engaged when pressure in chamber 40 increases sufficiently to displace diaphragm 45 in direction B and maintains the pressure in chamber 40.

Pressure plate 55 has a diameter less than the diameter of diaphragm 45 to allow for diaphragm portion 45a to be disposed between the edge of pressure plate 55 and housing 15. Pressure plate 55 includes an upwardly extending stop 55a positioned such that the top portion of stop 55a aligns with a vertical wall portion 15a of housing 15. This placement of stop 55a prevents excessive upward displacement of plate 55 greater than the surface area of diaphragm 45 (including portion 45a). In particular, as diaphragm 45 moves upward in direction B, pressure plate 55 is likewise displaced against spring 50 via spring plate 52b which eventually forces stop 55a to contact housing 15 at vertical wall 15a. Alternative stop mechanisms may be employed to prevent excessive movement of diaphragm 45 within chamber 41. As is evident from this description, the volume of chambers 40 and 41 change with movement of diaphragm 45 downward in direction A and upward in direction B. In particular, as the pressure increases in chamber 40 via sensing line 4, diaphragm 45 is forced upward in direction B, thereby increasing the volume of chamber 40 and decreasing the volume of chamber 41. Conversely, as the pressure decreases in chamber 40 via sensing line 4, diaphragm 45 moves downward in direction A, thereby decreasing the volume of chamber 40 and increasing the volume of chamber 41. Although the volume of chamber 41 may change, the pressure therein remains at atmosphere. In particular, bore 115 is present in wall 15a of housing 15 for venting the pressure in chamber 41 to atmosphere as diaphragm 45 moves in direction B. This allows the pressure in chamber 41 to remain at atmosphere and the source of the downward force applied to diaphragm 45 in direction A to be provided by spring 50.

Spring coil 50 is disposed between spring plates 52a, 52b. Adjustment screw 53 has a lower extending threaded portion 53a disposed through housing aperture 54 which contacts upper spring plate 52a. The lower extending portion 53a of adjustment screw 53 forces spring plate 52a downward in direction A providing a biasing force against coil spring 50 and spring plate 52b. The bias of spring coil 50 and the placement of pressure plate 55 may be adjusted via adjustment screw 53 based on the desired pressure regulation parameters provided by diaphragm 45 within chamber 41. In particular, by tightening adjustment screw 53, threaded portion 53a forces spring plate 52a against coil spring 50. The bias of spring 50 applies a force against spring plate 52b which forces pressure plate 55 in direction A against diaphragm 45. This displacement of diaphragm 45 downward in direction A is limited to the point where needle valve piston 20 engages seat 25. Similarly, by loosing adjustment screw 53, threaded portion 53a reduces the force against spring plate 52a and coil spring 50. This allows spring plate 52b, pressure plate 55 and diaphragm 45 to move upward in direction B. This displacement of diaphragm 45 upward increases the volume of chamber 40. By adjusting screw 53 and the force from spring 50 onto pressure plate 55, the response time associated with a pressure change received into chamber 40 and the corresponding displacement of diaphragm 45 may be modified.

Coupler 60 has a first end 60a and a second end 60b. First end 60a contacts spring plate 52b and receives the downward biasing force from coil spring 50. Coupler 60 extends through a bore centrally located in diaphragm 45 as well as a similarly aligned bore through pressure plate 55. Coupler 60 may have a threaded portion 63 which is used to hold coupler 60 in position through pressure plate 55 and diaphragm 45. Second end 60b of coupler 60 is connected to distal end 23 of pin 20 such that as diaphragm 45 is displaced in directions A or B, pin 20 is likewise displaced through the movement of coupler 60. U-shaped collar 72 is positioned around passageway 8 and includes a centrally located bore through which coupler 60 extends. The bore of u-shaped collar 72 may include o-rings 73 used to isolate the pump outlet pressure entering port 6 from the pressure in chamber 40. Obviously, various configurations may be employed to provide a coupling mechanism between diaphragm 45 and pin 20.

In operation, needle valve 9 bypasses pressurized gas from pump 1 away from surgical instrument 3 maintaining the system in a balanced state whereby sufficient pressure is supplied to or bypassed away from a patient's abdomen. In a balanced state, needle valve 9 and more particularly, pin 20 remains open or displaced from seat 25 allowing a portion of pressurized gas to bypass from inlet port 6 to outlet port 7 while also allowing a portion of the pressurized gas to be supplied to surgical instrument 3. Pressure from sensing line 4 is supplied to chamber 40. Diaphragm 45 senses this change in pressure. The pressure against diaphragm 45 is controlled by adjustment screw 53 in combination with the bias force from spring 50 and pressure plate 55. The change in pressure in chamber 40 either displaces diaphragm 45 in direction A or B. For example, if sensing line 4 provides an increase in pressure to chamber 40, diaphragm 45 moves in direction B biased against spring 50 and spring plates 52a, 52b. This increase in pressure indicates that a higher pressure level is in a patient's abdomen and that gas supplied by pump 1 needs to be diverted away or bypassed from surgical instrument 3. Displacement of diaphragm 45 in direction B lifts pin 20 further away from seat 25 thereby allowing more pressurized gas to flow from inlet port 6 through pathway 8 to outlet port 7. If sensing line 4 provides a decrease in pressure to chamber 40, diaphragm 45 moves in direction A biased away from spring 50 and spring plates 52a, 52b. This decrease in pressure indicates that a lower pressure level is present in a patient's abdomen and that additional pressurized gas needs to be supplied to surgical instrument 1. Displacement of diaphragm 45 in direction A pushes down on coupler 60 which moves pin 20. As pin 20 moves in direction A, angled central portion 21 engages seat 25 thereby restricting pathway 8 and preventing the flow of gas from inlet port 6 to outlet port 7. By restricting the bypass of pressurized gas through valve 10, more pressurized gas is supplied to a patient's abdomen via surgical instrument 3. In this manner, bypass valve 10 combines the pressure regulation feature of a diaphragm valve with the precise operation and control of a needle valve to regulate the flow of pressurized gas for surgical procedures.

Figure 3:
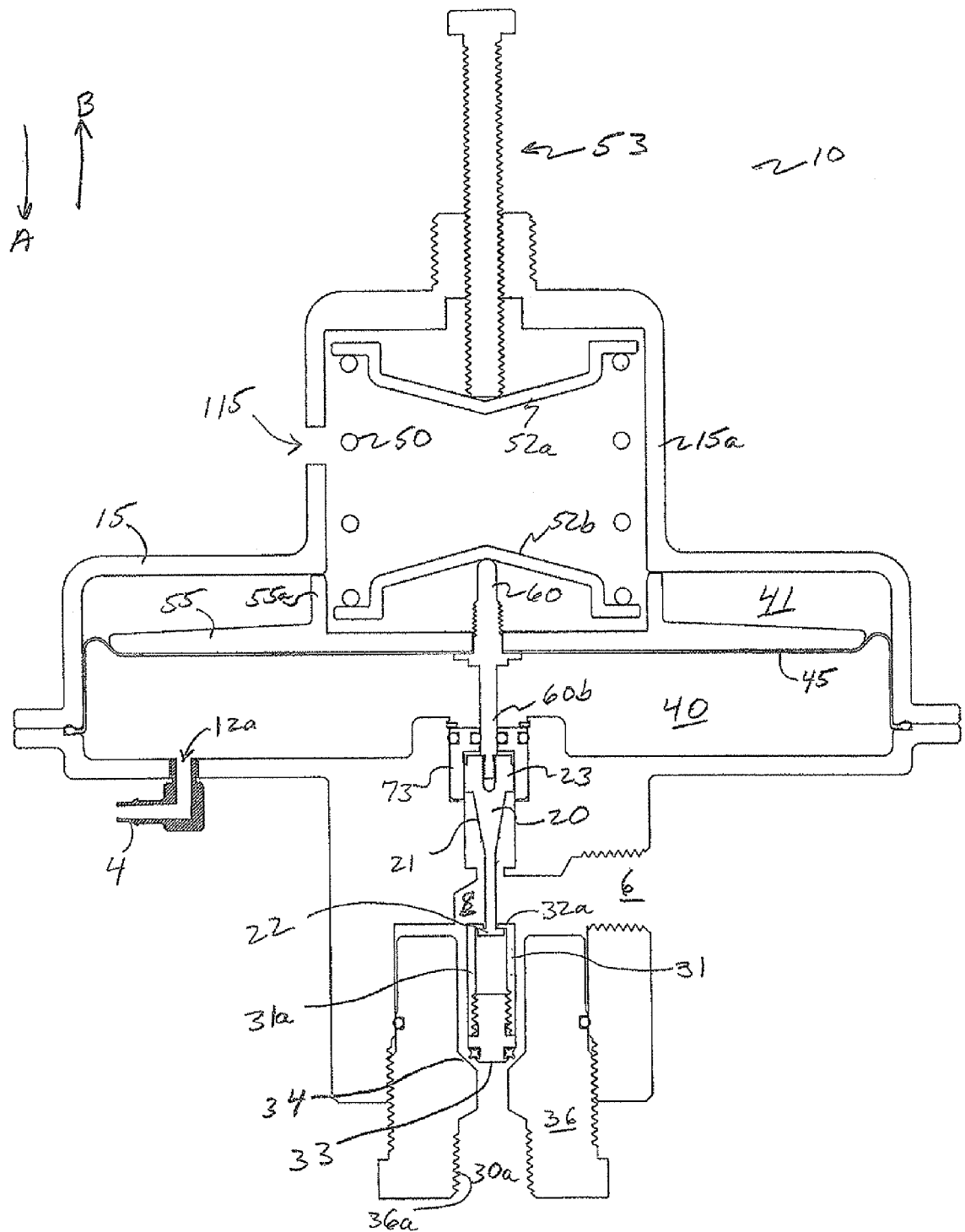
FIG. 3 illustrates a cross sectional view of a diaphragm controlled bypass valve in accordance with the present invention.

FIG. 3 is a schematic view of bypass valve 10 illustrating automatic relief mechanism assembly 30 in an open position due to movement of diaphragm 45 upward in direction B. Again, movement of diaphragm 45 in this manner indicates a significant increase in pressure supplied to a patient's abdomen requiring a rapid bypass of pressurized gas through bypass valve 10. As pressure in chamber 40 increases significantly, diaphragm 45 may be displaced in direction B a distance sufficient to engage diaphragm appendage portion 45a. As diaphragm 45 moves upward in direction B, stop 55a contacts vertical wall portion 15a. This upward movement of diaphragm 45 and pressure plate 55 pulls coupler 60 likewise upward, thereby pulling the proximal end 22 of pin 20 upward within piston 31. Vertical wall 31a of piston 30 includes clip portion 32a which extends inwardly and engages proximal end 22 of pin 20 which may have a T-shape configuration. This engagement of proximal end 22 and clip portion 32a pulls piston 31 upward in direction B which breaks the seal formed between transverse angled wall 33 of piston 31 and angled wall 34 of housing 36. This opens aperture 30a and allows additional pressurized gas to flow there through to atmosphere. Interior wall 36a of housing 36 may be threaded to receive a ¼" NPT connection to accommodate re-routing of the bypassed gas. In addition, since pin 20 is likewise pulled away from seat 25, pressurized gas is also bypassed through pathway 8 in addition to the gas flowing through automatic relief mechanism assembly 30. In this manner, an increase in pressurized gas in a patient's abdomen requiring rapid bypass is accommodated through the opening of the needle valve as well as the opening of aperture 30a of automatic relief mechanism assembly 30.

Figure 4:
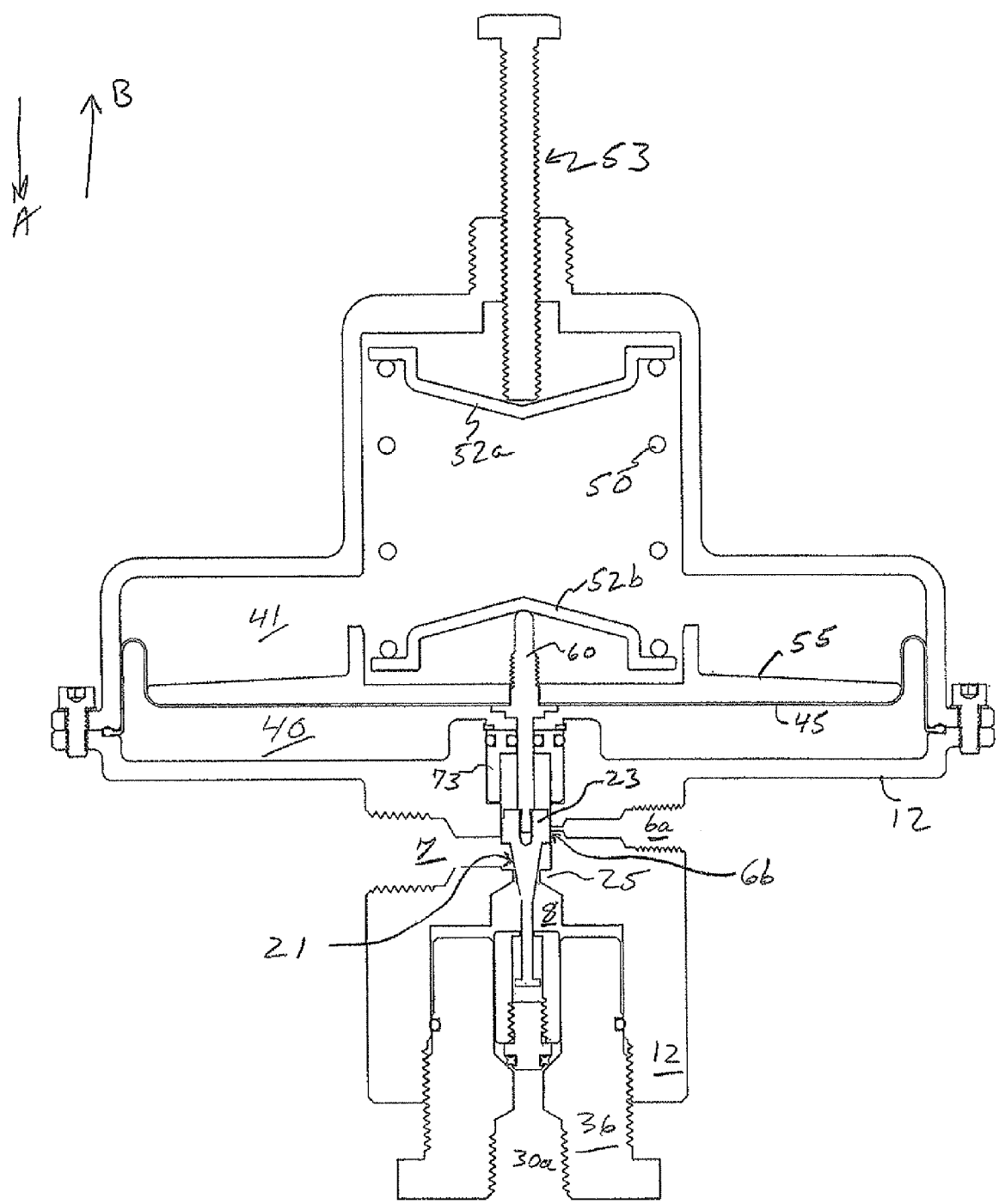
FIG. 4 illustrates a cross sectional view of a diaphragm controlled bypass valve in accordance with the present invention.
Figure 5:
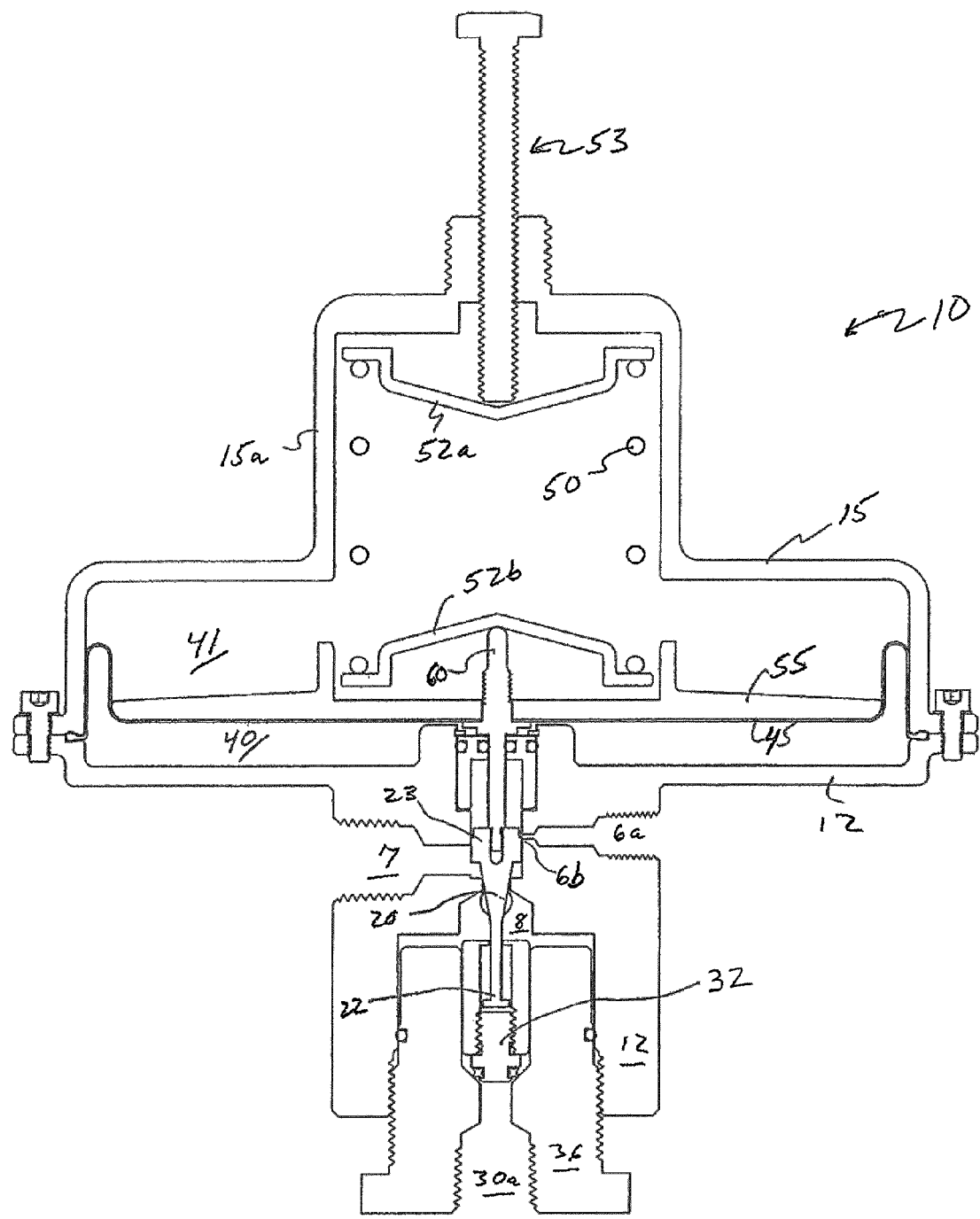
FIG. 5 illustrates a cross sectional view of a diaphragm controlled bypass valve in accordance with the present invention.

FIG. 4 illustrates a cross sectional side view of a diaphragm controlled bypass valve 10 turned 90° from that shown in FIG. 3. Needle valve portion 9 includes outlet port 7 and an additional inlet port 6a. Inlet ports 6 and 6a and outlet port 7 define the opening and closing of bypass valve 10 via valve pathway 8. As described with reference to FIG. 2 above, as angled portion 21 of needle pin 20 is displaced upward off seat 25, pressurized gas flows from input port 6 through pathway 8 to output port 7. In normal operation, pressurized gas within the system is sufficient to insufflate a patient's abdomen. Accordingly, additional gas provided via input port 6a is not needed and distal end 23 of pin 20 covers entry point 6b into valve pathway 8. However when a loss of gas within the closed system occurs, input port 6a is used to supply additional pressurized gas from within the system. For example, supply line 2 may be configured with a T-fitting to provide gas to both input ports 6 and 6a such that pressurized gas is supplied to pump 1. This is done, for example, when pressurized gas is suctioned out of the system during a surgical procedure and gas must be supplied to avoid malfunction of pump 1. When a loss of pressure in a patient's abdomen occurs, pressure in chamber 40 decreases which forces diaphragm 45 in direction A forcing pin 20 to close and engage seat 25 as illustrated in FIG. 5. The movement of pin 20 and distal end 23 in direction A reveals entry point 6b for the gas supplied via port 6a to enter pathway 8 of valve 10.

Figure 6:
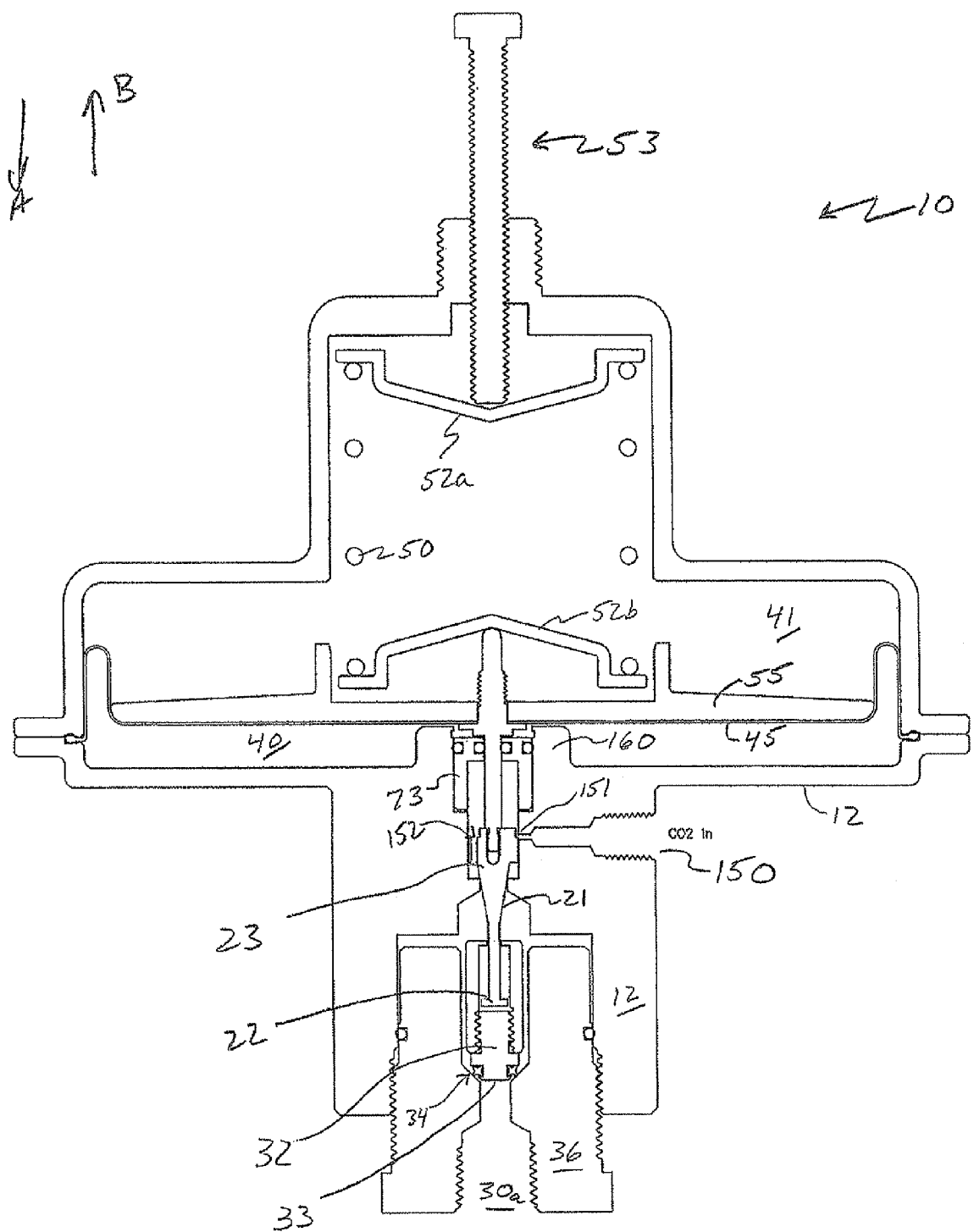
FIG. 6 illustrates a cross sectional view of a diaphragm controlled bypass valve in accordance with the present invention.

FIG. 6 illustrates a cross sectional side view of a diaphragm controlled bypass valve 10 having an external gas port 150 used to accommodate a loss of gas within the closed system. External gas port 150 is disposed through housing 12 to communicate with valve pathway 8 to provide additional gas to the system. Because the system is closed, only a certain amount of $CO_2$ gas is provided from pump 1 to balance the system. In particular, a certain amount of gas is bypassed through valve 10 and a certain amount of gas is provided to surgical instrument 3 from pump 1. When a significant decrease in pressure occurs, additional gas may be needed to return the system to a balanced state. For example, when $CO_2$ gas is suctioned from a patient's abdomen, the pressure may drop from approximately 12 mmHG to approximately 4 mmHG. This suctioned gas is no longer contained within the system and corresponds to a pressure decrease in chamber 40 as sensed via sensing line 4 which displaces diaphragm 45 downward in direction A to engage lower stop 160 of housing 12. This pushes angled portion 21 of pin 20 against valve seat 25 which prevents gas flow from inlet port 6 to outlet port 7 through pathway 8 and likewise forces lower portion 23 downward to engage plug 32 against angled seat 34 to close aperture 30a. This downward displacement provides a small opening 151 into pathway 8 near distal end 23 of pin 20 which allows additional gas to be introduced into the system through external gas port 150. Port 150 is positioned above inlet port 6 and orthogonal to port 6a through needle valve housing 12. The difference between port 6a shown in FIG. 5 and port 150 shown in FIG. 6 is that port 6a provides gas that is already within the closed system via a T-fitting and port 150 is connected to an external $CO_2$ source to supply additional gas from outside the system into a patient's abdomen. The width of distal end 23 of pin 20 is less then the width of valve pathway 8 providing a channel 152. This allows gas received via inlet port 150 to feed into pathway 8, around distal end 23 of pin 20.

Figure 7:
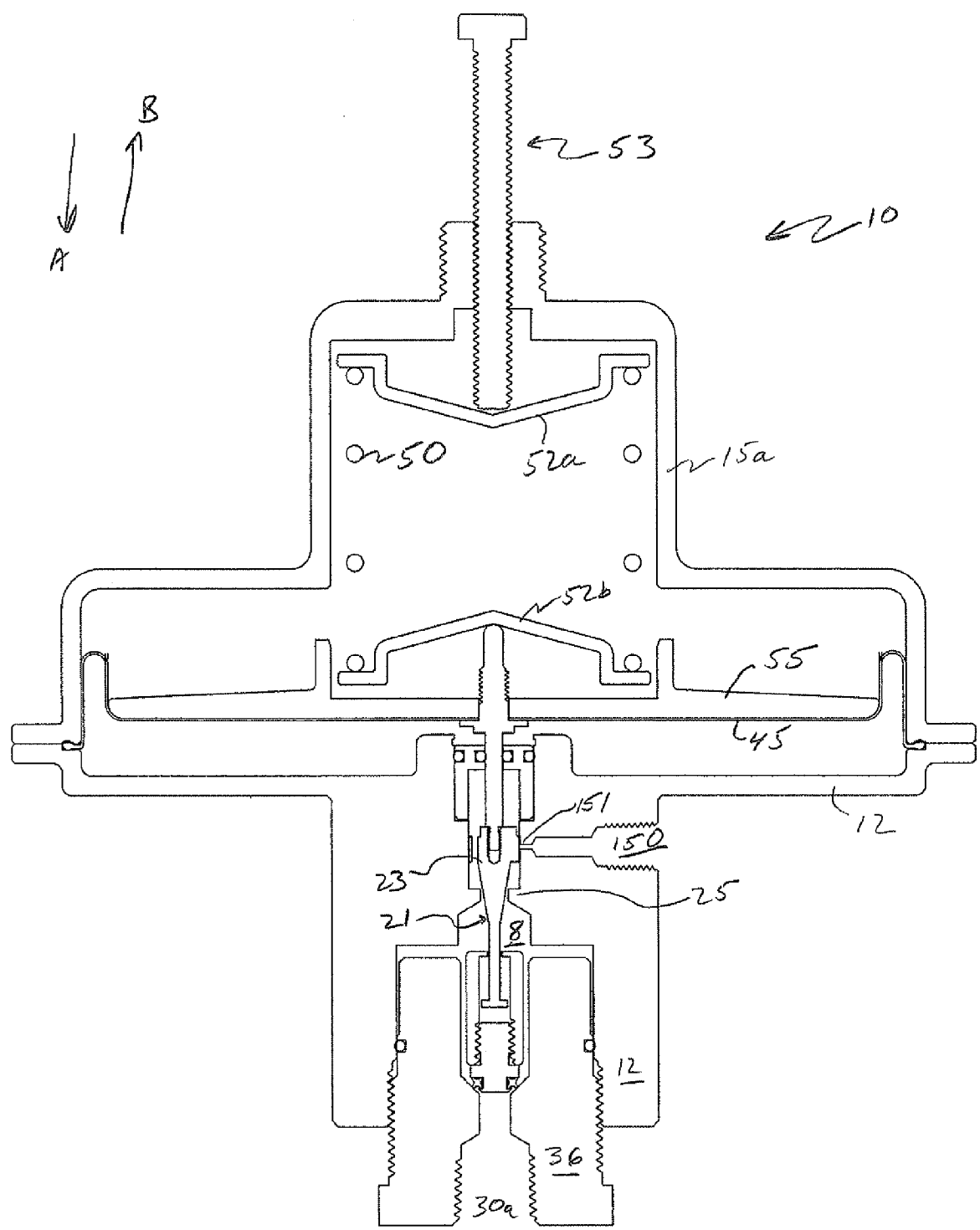
FIG. 7 illustrates a cross sectional view of a diaphragm controlled bypass valve in accordance with the present invention

As shown in FIG. 7, in a balanced state, needle valve 9 and more particularly, angled central portion 21 of pin 20 remains open or displaced from seat 25 allowing a portion of pressurized gas to bypass from inlet port 6 to outlet port 7 while also allowing a portion of the pressurized gas to be supplied to surgical instrument 3. As angled portion 21 maintains its position off of seat 25, distal end 23 of pin 20 blocks opening 151 of inlet port 150 thereby preventing introduction of additional pressurized $CO_2$ gas into the system.

While the present invention has been disclosed with reference to certain embodiments, numerous modifications, alterations and changes to the described embodiments are possible without departing from the sphere and scope of the present invention, as defined in the appended claims. Accordingly, it is intended that the present invention not be limited to the described embodiments, but that it has the full scope defined by the language of the following claims, and equivalents thereof.

What is claimed is:

1. A diaphragm controlled bypass valve comprising:
a first valve housing having an inlet, a first outlet and a first flow pathway defined between said inlet and said first outlet;
a needle valve pin disposed at least partially within said first flow pathway, said needle valve pin having an open position in which flow is allowed between the inlet and the first outlet;
a valve seat disposed within said first valve housing configured to receive a portion of said needle valve pin to close said first flow path;
a second valve housing connected to said first valve housing;
a diaphragm extending radially within said second valve housing, said diaphragm and said second valve housing defining a first chamber there between;
a second pressure chamber defined between said diaphragm and said first valve housing;
a second flow path defined from said inlet to a second outlet, said second flow path exposed when said needle valve pin is in said open position;
a relief housing threadedly engaged within said second outlet; and
a relief piston disposed within said relief housing and communicating with a lower section of said needle valve pin, said relief piston configured to open and close said second flow path.

2. The diaphragm controlled bypass valve of claim 1 wherein said relief housing comprises an external housing threadedly engaged at least partially within said first valve housing.

3. The diaphragm controlled bypass valve of claim 2 wherein said relief housing comprises a seat configured to receive a portion of said relief piston to open and close said second flowpath.

4. The diaphragm controlled bypass valve of claim 3 wherein said relief piston comprises a plug disposed at a lower end of said relief piston configured in a first position to engage said relief housing seat to close said second flowpath and a second position displaced a distance from said seat to open said second flowpath.

5. The diaphragm controlled bypass valve of claim 1 further comprising a pressure plate disposed within said second valve housing and in contact with said diaphragm.

6. The diaphragm controlled bypass valve of claim 5 further comprising:
a first and second spring plates positioned within said second valve housing; and
a coil spring disposed between said first and second spring plates, said coil spring and said first spring plate supplying a bias force against said pressure plate and said diaphragm.

7. The diaphragm controlled bypass valve of claim 6 further comprising an adjustment mechanism positioned through a bore in said second valve housing and in contact with said second spring plate, said adjustment mechanism configured to apply a force against said diaphragm via said first spring plate and said pressure plate.

8. The diaphragm controlled bypass valve of claim 5 wherein said pressure plate having a first diameter and said diaphragm having a second diameter, said first diameter less than said second diameter.

9. The diaphragm controlled bypass valve of claim 1 wherein said relief piston is defined by a vertical wall, a transverse angled lower wall and a cavity therebetween, at least a portion of said lower section of said needle valve pin disposed within said cavity.

10. The diaphragm controlled bypass valve of claim 9 wherein said vertical wall further comprises a clip portion disposed inwardly toward said cavity, said clip portion configured to contact said lower section of said needle valve pin when said valve is in a fully open position.

11. The diaphragm controlled bypass valve of claim 1 wherein said first valve housing includes a vertically extending stop communicating with said diaphragm within said first chamber.

12. A diaphragm controlled bypass valve comprising:
a first valve housing having an inlet, a first outlet and a first flow pathway defined between said inlet and said first outlet;
a needle valve pin disposed at least partially within said first flow pathway, said needle valve pin having an open position in which flow is allowed between the inlet and the first outlet;
a valve seat disposed within said first valve housing configured to receive a portion of said needle valve pin to close said first flow path;
a second valve housing connected to said first valve housing;
a diaphragm extending radially within said second valve housing, said diaphragm and said second valve housing defining a first chamber there between;
a second pressure chamber defined between said diaphragm and said first valve housing;
a second flow path defined from said inlet to a second outlet, said second flow path exposed when said needle valve pin is in said open position;
wherein said inlet port is a first inlet, said valve further comprising a second inlet port disposed through said first valve housing and communicating with said first pathway, said second inlet port configured to provide a third flowpath when said valve seat engages said needle valve pin.

13. The diaphragm controlled bypass valve of claim 12 further comprising a third inlet port disposed through said first valve housing, said third inlet port configured to supply pressurized gas to said first pathway.

14. The diaphragm controlled bypass valve of claim 12 further comprising a third inlet port disposed through said first valve housing and communicating with said first pathway, said third inlet port configured to provide a fourth flowpath when said valve seat engages said needle valve pin.

* * * * *